United States Patent [19]

Edington et al.

[11] 4,271,304
[45] Jun. 2, 1981

[54] PYRIDINE DERIVATIVES

[75] Inventors: Edwin T. Edington, Cookham; Alan C. White, Windsor, both of England

[73] Assignee: John Wyeth & Brother, Ltd., Taplow, England

[21] Appl. No.: 37,594

[22] Filed: May 9, 1979

[30] Foreign Application Priority Data

May 30, 1978 [GB] United Kingdom ............... 24123/78

[51] Int. Cl.$^3$ .................. C07D 213/68; C07D 213/89
[52] U.S. Cl. .................... 546/290; 546/270; 546/301; 546/302; 546/303; 424/263
[58] Field of Search ............... 546/290, 270, 301, 302, 546/303

[56] References Cited

PUBLICATIONS

Shaw, J. Am. Chem. Soc. 1949, vol. 71, pp. 67–70.
Schöllkopf et al., Ann. Chem. 1972, vol. 765, pp. 153–170.
Litster et al., J. Am. Chem. Soc. 1968, vol. 90, pp. 4362–4366.
Renshaw et al., J. Am. Chem. Soc. 1937, vol. 59, pp. 297–301.
Dinan et al., J. Org. Chem. 1964, vol. 29, pp. 1650–1652.
Gardner et al. J. Chem. Soc. 1957, pp. 4375–4385.
Chem. Abst. 1947–1978, Subject Index Pages, vols. 41–89.
Hill et al., J. Org. Chem. 1949, vol. 14, pp. 783–788.
Schöllkopf et al., Tetrahedron Letter, 1970, No. 52, pp. 4527–4530.
Schöllkopf et al., Chem. Abst. 1973, vol. 78, No. 110284p.

*Primary Examiner*—Henry R. Jiles
*Assistant Examiner*—Natalia Harkaway
*Attorney, Agent, or Firm*—Arthur E. Wilfond

[57] ABSTRACT

Pyridine derivatives having the formula

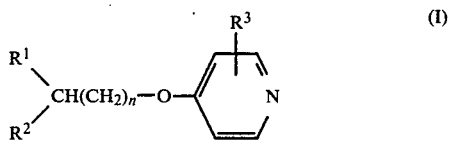

and their N-oxides and pharmaceutically acceptable acid addition salts, wherein $R^1$ and $R^2$ are independently aryl, $R^3$ is hydrogen or lower alkyl and n is 0, 1 or 2, have CNS activity and may be used as antidepressants.

6 Claims, No Drawings

PYRIDINE DERIVATIVES

The invention relates to novel pyridine derivatives which show pharmaceutical activity, particularly CNS activity. The invention provides the new pyridine derivatives, processes for their preparation and pharmaceutical compositions containing the new pyridine derivatives.

The invention provides novel pyridine derivatives having the formula I

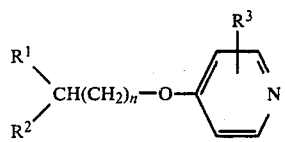

and their N-oxides and pharmaceutically acceptable acid addition salts, wherein $R^1$ and $R^2$ are independently aryl, $R^3$ is selected from hydrogen and lower alkyl and n is selected from 0, 1 and 2.

By the term "lower" as used herein in connection with such groups as alkyl, alkylene and alkoxy, there is meant that the group contains up to 6 carbon atoms, preferably up to 4 carbon atoms.

$R^1$ and $R^2$ may be the same or different aryl groups. The aryl groups may be selected from unsubstituted phenyl and naphthyl and phenyl and naphthyl substituted by one to two substituents selected from halogen, lower alkyl, lower alkoxy, lower alkylenedioxy and trifluoromethyl. As examples of such substituents there may be mentioned fluorine, chlorine, bromine, methyl, ethyl, propyl, butyl, methoxy, ethoxy, propoxy, butoxy, methylenedioxy and trifluoromethyl. The aryl group preferably has a monocyclic aromatic ring, i.e. phenyl or substituted phenyl, but may be bicyclic, for instance, naphthyl or substituted naphthyl. $R^1$ and $R^2$ are preferably phenyl. $R^3$ is hydrogen or lower alkyl, for example methyl, ethyl, propyl and butyl. $R^3$ is preferably hydrogen or methyl. The symbol n represents 0, 1 or 2, preferably 0 or 1, advantageously 0.

A preferred class of compounds are the N-oxides of compounds having formula I where $R^1$ and $R^2$ are independently selected from phenyl and phenyl substituted by one to two substituents selected from halogen, lower alkyl, lower alkoxy, lower alkylenedioxy and trifluoromethyl, $R^3$ is hydrogen and n is 0.

The invention may be particularly illustrated by 4-(diphenylmethoxy)-pyridine, its acid addition salts and its N-oxide and 4-(2,2-diphenylethoxy)pyridine, its acid addition salts and its N-oxide.

The invention also provides a process for the preparation of a compound having the formula I or an N-oxide or pharmaceutically acceptable acid addition salt thereof, wherein (a) a salt containing a substituted alkoxide ion having the formula

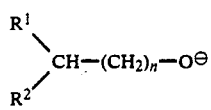

(wherein $R^1$, $R^2$ and n are as defined above) is reacted with a pyridine derivative having the formula

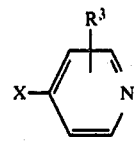

(wherein $R^3$ is as defined above and X is an atom or group replaceable by nucleophilic attack by the substituted alkoxide ion) or the N-oxide thereof; or (b) a compound having formula I is converted into its N-oxide by oxidation; or (c) an N-oxide of a compound having formula I is converted into a compound having formula I by reduction.

The starting materials for method (a) are known or, where new, can be prepared in known manner. The starting material for method (b) or (c) can be prepared by method (a). The process of the invention should normally avoid strong acid conditions because such conditions may lead to decomposition of the product.

In method (a) the leaving group or atom X may be, for example, halogen such as chlorine or bromine, phenoxy or nitro. In particular we prefer to use compounds having the formula

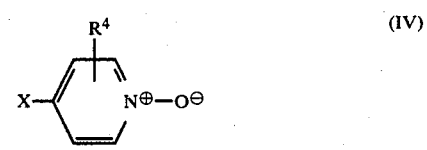

where x is nitro or chlorine, where an N-oxide is employed, or compounds having the formula

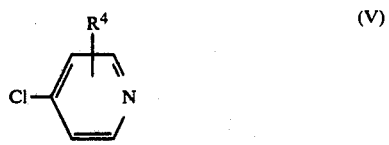

where the pyridine derivative itself is used. The other reactant used, the salt containing the substituted alkoxide ion is normally prepared in situ from the alcohol having the formula

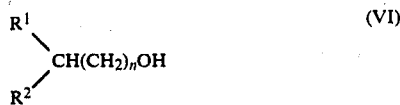

For instance the sodium salt may be prepared by adding sodium hydride to the alcohol in the reaction mixture. The reaction of the salt with the pyridine derivative of formula IV or its N-oxide may be carried out under reaction conditions conventional for the preparation of ethers by nucleophilic attack with alkoxides.

Method (b) may be carried out by using a compound having formula I made by method (a) using a pyridine derivative of formula III. The compound having formula I may be converted into its N-oxide in known manner.

Method (c) may be carried out by using an N-oxide obtained by method (a) using an N-oxide of the pyridine derivative of formula III. The reduction according to method (c) may be carried out in known manner, in particular by catalytic hydrogenation. Raney nickel may be used as catalyst for the hydrogenation.

The compounds having formula I and their N-oxides and pharmaceutically acceptable acid addition salts are indicated for pharmaceutical use. In particular they show CNS (central nervous system) activity, when tested on warm blooded animals. They reverse the hypothermia induced by reserpine on mice and thus may have potential use as antidepressant drugs. For example, the compound of Example 1 shows activity against reserpine-induced hypothermia at 10 milligrams per kilogram (p.o.) and the compounds of Examples 2 and 3 show such activity at 100 milligrams per kilogram (p.o.).

The invention also includes pharmaceutical compositions containing as active ingredient a compound of formula I or a pharmaceutically acceptable acid addition salt thereof which may be micronised if desired. In addition to the active ingredient said compositions also contain a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80%, by weight of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with an encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, a sterile organic solvent or a mixture of both. Preferably a liquid carrier is one suitable for parenteral injection. Where the active ingredient is sufficiently soluble it can be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example, packeted powders or vials or ampoules. The unit dosage form can be a capsule, cachet or tablet itself, or it can be the appropriate number of any of these in package form. The quantity of active ingredients in a unit dose of composition may be varied or adjusted from 5 mg or less to 500 or more, according to the particular need and the activity of the active ingredient. The invention also includes the compounds in the absence of carrier where the compounds are in unit dosage form.

The following Examples illustrate the invention:

EXAMPLE 1

4-(Diphenylmethoxy)pyridine-1-oxide

Diphenylmethanol (18.4 g, 0.1 m) was added portionwise to a suspension of sodium hydride (2.4 g, 0.1 m) in dimethylformamide (300 ml) under nitrogen. After the reaction had ceased, the suspension was treated dropwise with a solution of 4-nitropyridine-1-oxide (14 g, 0.1 m) in dimethylformamide (500 ml). This caused the colour of the mixture to change from orange to dark blue. After a further twelve hours at room temperature, the mixture was filtered and evaporated under reduced pressure, leaving a residue that crystallised from toluene giving 19.8 g of 4-[diphenylmethoxy]pyridine-1-oxide as light yellow crystals, m.pt. 155°–157° C.

Microanalysis:

Found: C, 78.6%; H, 5.65%; N, 5.1%. $C_{18}H_{15}NO_2$ requires C, 78.0%; H, 5.41%; N, 5.05%.

EXAMPLE 2

4-Diphenylmethoxypyridine

4-Diphenylmethoxypyridine-1-oxide (5.0 g; 0.018 m) was hydrogenated in ethanol (100 ml) at a pressure of 2 atmospheres using 5 g, of freshly alcohol washed Crosfield Raney nickel. After two hours at room temperature the mixture was filtered, and the solvent removed, leaving an oil that crystallised from petrol (60–80) to give 3.05 g of 4-diphenylmethoxypyridine as white crystals, m.pt. 68°–70° C.

Microanalysis:

Found: C, 82.9%; H, 6.0%; N, 5.3%. $C_{18}H_{15}NO$ requires C, 82.73%; H, 5.79%; N, 5.36%.

EXAMPLE 3

4-(2,2-Diphenylethoxy)-pyridine-1-oxide 2,2-diphenylethanol (4 g, 0.02 m) was added portionwise to a suspension of sodium hydride (0.48 g, 0.02 m) in dry dimethylformamide (200 ml) under nitrogen. After the reaction had ceased, the mixture was added dropwise to a solution of 4-nitropyridine-1-oxide (2.8 g, 0.02 m) in dry dimethylformamide (100 ml) at 35°–40° C. The mixture was maintained at this temperature for 12 hours and then filtered. The solvent was removed under reduced pressure, leaving a residue that was heated with successive portions of toluene. The toluene solution was evaporated to an oil which was crystallised from a mixture of toluene and 60–80 petrol (1:1). This gave 4-(2,2-diphenylethoxy)pyridine-1-oxide (2.2 g) as orange crystals, m.pt. 134°–138° C.

Microanalysis:

Found: C, 76.2%; H, 6.6%; N, 4.5%. $C_{19}H_{17}NO_2 \cdot \frac{1}{2}H_2O$ requires C, 75.98%; H, 7.2%; N, 4.66%.

EXAMPLE 4

In a manner similar to Examples 1 and 3 the following alcohols and pyridine derivatives are used to give the indicated products.

| Alcohol | Pyridine Derivative | Product |
|---|---|---|
| 3,3-Diphenyl-1-propanol | 4-Nitro-pyridine-1-oxide | 4-(3,3-Diphenylpropoxy)-pyridine-1-oxide |
| Di(4-chlorophenyl)methanol | 2-Methyl-4-nitropyridine-1-oxide | 4-[Di(4-chlorophenyl)methoxy]-2-methyl-pyridine-1-oxide |
| α-(5-Bromo-2-naphthyl)benzyl alcohol | 4-Nitro-pyridine-1-oxide | 4-[α-(5-Bromo-2-naphthyl)benzyloxy]-pyridine-1-oxide |
| Di(4-ethoxyphenyl)methanol | 4-Nitro-pyridine-1-oxide | 4-[Di(4-ethoxyphenyl)methoxy] pyridine-1-oxide |
| α-(2-Tolyl)benzyl alcohol | 4-Nitro-pyridine-1-oxide | 4-[α-(2-Tolyl)benzyloxy]-pyridine-1-oxide |
| α-(3,4-Methylenedioxyphenyl)benzyl alcohol | 4-Nitro-pyridine-1-oxide | 4-[α-(3,4-Methylenedioxyphenyl)benzyloxy]-pyridine-1-oxide |
| α-(3,5-Dibromophenyl)benzyl alcohol | 4-Nitro-pyridine-1-oxide | 4-[α-(3,5-Dibromophenyl)benzyloxy]-pyridine-1-oxide |
| Di(3-trifluoromethylphenyl)methanol | 4-Nitro-pyridine-1-oxide | 4-[Di(3-trifluoromethylphenyl)methoxy]-pyridine-1-oxide |
| Di(4-Fluorophenyl)methanol | 4-Nitro-pyridine-1-oxide | 4-[Di(4-fluorophenyl)methoxy]-pyridine-1-oxide |
| Di(1-naphthyl)methanol | 4-Nitro-pyridine-1-oxide | 4-[Di(1-naphthyl)methoxy]-pyridine-1-oxide |

We claim:

1. A compound selected from those having the formula

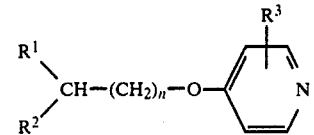

and their N-oxides and pharmaceutically acceptable acid addition salts, wherein $R^1$ and $R^2$ are independently selected from unsubstituted phenyl and naphthyl and phenyl and naphthyl substituted by one to two substituents selected from halogen, lower alkyl, lower alkoxy, lower alkylenedioxy and trifluoromethyl, excluding sterically impossible embodiments thereof; $R^3$ is selected from hydrogen and lower alkyl and n is selected from 0, 1 and 2.

2. A compound selected from those having the formula

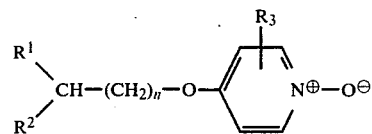

and their pharmaceutically acceptable acid addition salts, wherein $R^1$ and $R^2$ are independently selected from unsubstituted phenyl and naphthyl and phenyl and naphthyl substituted by one to two substituents selected from halogen, lower alkyl, lower alkoxy, lower alkylenedioxy and trifluoromethyl, excluding sterically impossible embodiments thereof; $R^3$ is selected from hydrogen and lower alkyl and n is selected from 0, 1 and 2.

3. A compound as defined in claim 2, wherein $R^3$ is hydrogen and n is 0.

4. A compound as defined in claim 2, which is 4-(diphenylmethoxy)pyridine-1-oxide.

5. A compound as defined in claim 2, which is 4-(2,2-diphenylethoxy)pyridine-1-oxide.

6. A compound as defined in claim 1, which is 4-(diphenylmethoxy)pyridine or a pharmaceutically acceptable acid addition salt thereof.

* * * * *